US00PP11790P2

(12) United States Plant Patent
Ruigrok

(10) Patent No.: US PP11,790 P2
(45) Date of Patent: Feb. 27, 2001

(54) DAHLIA PLANT NAMED 'LISA BURGUNDY'

(76) Inventor: Frank N. G. Ruigrok, Hyacintenlaan 15, 2182 DE Hillegom (NL)

( * ) Notice: Subject to any disclaimer, the term of this patent is extended or adjusted under 35 U.S.C. 154(b) by 0 days.

(21) Appl. No.: 09/233,133

(22) Filed: Jan. 19, 1999

(30) Foreign Application Priority Data

Oct. 28, 1997 (NL) ..... DHL 92

(51) Int. Cl.[7] ..... A01H 5/00
(52) U.S. Cl. ..... Plt./321
(58) Field of Search ..... Plt./321

(56) References Cited

U.S. PATENT DOCUMENTS

P.P. 11,406 * 6/2000 Verwer ..... Plt./321

OTHER PUBLICATIONS

Broertjes et al., Mutation Breeding of *Dahlia variabilis*, Euphytica, 16(2):171–176, 1967.*
Boyer et al., American Dahlia Society 1976–1989 List of Dahlias, pp. 1–2, 43 and 125, 1989.*
Das et al., New Dahlias Through Irradiation, Indian Horticulture, 23(1):19 and 21, 1978.*
Gottschalk et al., Induced Mutations in Plant Breeding, pp. 30–31 and 67–67, 1983.*
GTITM UPOVROM Citation for 'Lisa' as per NL PBR DHL0016; Jan. 18, 1993.*
GTITM UPOVROM Citation for 'Lisa' as per QZ PBR 952490; Feb. 22, 1996.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Dahlia plant named 'Lisa Burgundy', characterized by its large and numerous double inflorescences that are about 8.2 cm in diameter; dark reddish purple ray florets; mostly upright, mounded and uniform growth habit; dark green leaves; and strong peduncles that hold inflorescences about the foliage.

1 Drawing Sheet

BACKGROUND OF THE INVENTION

The present invention relates to a new and distinct variety of Dahlia plant, botanically known as *Dahlia variabilis*, and hereinafter referred to by the cultivar name 'Lisa Burgundy'.

The new Dahlia is a naturally-occurring whole plant mutation of the *Dahlia variabilis* cultivar 'Lisa', not patented. The new Dahlia was discovered by the Inventor in September, 1996 in a controlled environment in Hillegom, The Netherlands, within a population of plants of 'Lisa'. The selection of this plant was based on its unqiue ray floret color.

Asexual reproduction of the new Dahlia by terminal cuttings harvested in Hillegom, The Netherlands, has shown that the unique features of this new Dahlia are stable and reproduced true to type in successive generations.

BRIEF SUMMARY OF THE INVENTION

The new Dahlia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Lisa Burgundy'. Those characteristics in combination distinguish 'Lisa Burgundy' as a new and distinct cultivar:

1. Large and numerous double inflorescences that are about 8.2 cm in diameter.

2. Dark reddish purple ray florets.
3. Mostly upright, mounded and uniform growth habit.
4. Dark green leaves.
5. Strong peduncles that hold inflorescences above the foliage.

Compared to plants of the parent cultivar, 'Lisa', plants of the new Dahlia have dark red purple ray florets whereas plants of the cultivar 'Lisa' have light pink ray florets. In addition, ray floret color of plants of the new Dahlia does not fade with development, whereas ray floret color of plants of the cultivar 'Lisa' fades significantly with development. Compared to plants of the cultivar 'Lisa Dark Pink', disclosed in U.S. Plant patent application Ser. No. 09/233,134, in side-by-side comparisons conducted in De Lier, The Netherlands, plants of the new Dahlia are more freely-flowering and differ in ray floret color. Compared to plants of the culitvar 'Lisa Pearl', disclosed in U.S. Plant patent application Ser. No. 09/233,135, in side-by-side comparisons conducted in De Lier, The Netherlands, plants of the new Dahlia are broader, have larger leaves, and differ in ray floret color.

BRIEF DESCRIPTION OF THE PHOTOGRAPH

The accompanying colored photograh illustrates the overall appearance of the new cultivar, showing the colors as true as it is reasonably possible to obtain in colored reproductions of this type. Colors in the photograph may differ from the color values cited in the detailed botanical description which accurately describe the actual colors of the new Dahlia. The photograph comprises a top perspective view of a typical plant of the new Dahlia.

DETAILED BOTANICAL DESCRIPTION

In the following description, color references are made to The Royal Horticultural Society Colour Chart except where general terms of ordinary dictionary significance are used. The following observations and measurements describe plants grown in De Lier, The Netherlands, in 12-cm containers in a glass greenhouse with average day and night temperatures of 22 and 18° C., respectively. Plants were about 8 to 10 weeks old after planting.

Botanical classification: *Dahlia variabilis*, 'Lisa Burgundy'.

Parentage: Naturally-occuring whole plant mutation of *Dahlia variabilis*, cultivar 'Lisa', not patented.

Propagation:

*Type.*—By terminal cuttings.

*Time to initiate roots.*—Summer: About 5 days at 22° C. Winter: About 8 days at 20° C.

*Time to develop roots.*—Summer: About 12 days at 22° C. Winter: About 16 days at 20° C.

*Rooting habit and root description.*—Easily propagated; roots fine, fibrous and well-branched.

Plant description:

*Appearance.*—Typically grown as potted flowering plants. Mostly upright, mounded and uniform growth habit; rounded plant apex. Moderate growth rate and moderately vigorous. Appropriate for 10 to 12.5-cm containers. Plants typically flower about 8 weeks after planting rooted cuttings. Freely basally branching, however, plants typically require pinching to enhance lateral branch development.

*Plant height.*—About 28 cm.

*Plant spread.*—About 33 cm.

*Stem description.*—Lateral branch diameter: About 1.3 cm. Internode length: About 3.8 cm. Texture: Smooth. Color: 144A.

*Foliage description.*—Arrangement: Young foliage, leaves single; fully expanded foliage, leaves compound, trifoliate; opposite. Leaf length: About 18 cm. Leaf width: About 14.5 cm. Terminal leaflet length: About 10 cm. Terminal leaflet width: About 5.5 cm. Leaflet shape: Ovate. Leaflet apex: Acute. Leaflet base: Attenuate. Leaflet margin: Dentate. Leaflet texture: Glabrous. Petiole length: About 6.5 cm. Color: Young leaflets, upper surface: Greener than 147A. Young leaflets, lower surface: Lighter than 147B. Mature leaflets, upper surface: 147A. Mature leaflets, lower surface: Lighter than 147B. Petiole: 144A.

Flowering description:

*Appearance.*—Double inflorescence form. Inflorescences generally hemispherical and borne on terminals above foliage, arising from leaf axils on strong peduncles; inflorescences above the foliage. Inflorescences face upright and outward. Freely flowering, typically about 25 inflorescences per plant. Disc and ray florets arranged acropetally on a capitulum. Not fragrant.

*Flowering response.*—Under natural conditions, plants flower intermittently from late spring through fall.

*Inflorescence longevity.*—Inflorescences typically maintain good substance for about 1 to 2 weeks on the plant.

*Flower bud* (*just before opening*).—Shape: Flattened spherical. Length: About 1 cm. Diameter: About 1.25 cm. Color: 143A to 144A.

*Inflorescence size.*—Diameter: About 8.2 cm. Depth (height): About 2.4 cm. Disc floret diameter: About 1 cm; conspicuous only on fully opened inflorescences.

*Ray florets.*—Quantity per inflorescence: About 73. Shape: Broadly elliptic. Orientation: Initially upright to horizontal; cupped. Length: About 3.8 cm. Width: About 2.2 cm. Apex: Acute, emarginate, bifid or trifid. Base: Attenuate. Margin: Entire. Texture: Velvety, glabrous. Color: When opening, upper surface: 61A to 58A. When opening, lower surface: 61A with light pink, 62C to 62D, longitudinal veins. Fully opened, upper surface: 59C to 60B. Fully opened, lower surface: 61A to 61B with light pink, 62C to 62D, longitudinal veins.

*Disc florets.*—Quantity per inflorescence: About 27. Shape: Tubular. Orientation: Upright. Length: About 1 cm. Width: Apex: About 3 mm. Base: About 1.5 mm. Apex: Pentafid. Color: Apex: 9A. Mid-section: 17A. Base: Greenish white.

*Peduncle.*—Aspect: Upright and strong. Length: About 15 cm. Diameter: About 4 mm. Texture: Smooth. Color: 144A.

*Involucral bracts.*—Shape: Oblong to linear. Tip: Acute to rounded. Margin: Entire. Texture: Waxy. Color: 144A to 144B.

*Reproductive organs.*—Androecium: Present on disc florets only. Anther color: 9A. Pollen amount: Moderate. Pollen color: 17A. Gynoecium: Present on disc and ray florets.

Disease resistance: Resistance to known Dahlia diseases has not been observed on plants grown under commercial greenhouse conditions.

Seed production: Seed production has not been observed.

It is claimed:

1. A new and distinct cultivar of Dahlia plant named 'Lisa Burgundy', as illustrated and described.

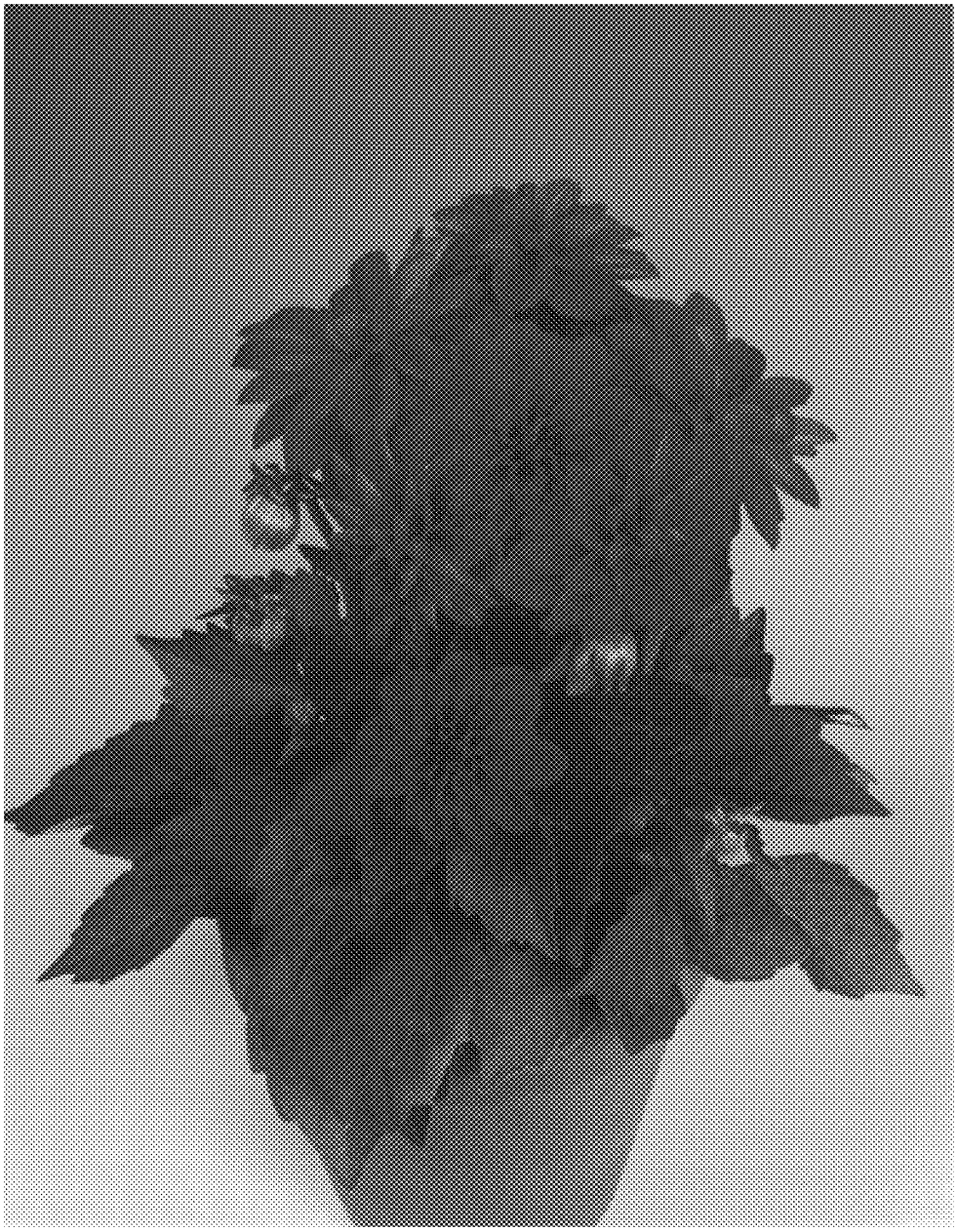

* * * * *